United States Patent

Bednar

[11] Patent Number: 6,078,283
[45] Date of Patent: Jun. 20, 2000

[54] REMOTE SEISMIC DATA ACQUISITION UNIT WITH COMMON RADIO AND GPS ANTENNA

[75] Inventor: Eugene David Bednar, Houston, Tex.

[73] Assignee: Input/Output, Inc., Stafford, Tex.

[21] Appl. No.: 08/961,831

[22] Filed: Oct. 31, 1997

[51] Int. Cl.[7] .............................. G01S 05/00; G01V 1/22
[52] U.S. Cl. .................. 342/357.13; 701/213; 367/77
[58] Field of Search .............. 342/357, 357.13; 701/213; 367/77; 455/132, 269

[56] References Cited

U.S. PATENT DOCUMENTS

| | | | |
|---|---|---|---|
| 4,030,100 | 6/1977 | Perrotti | 343/709 |
| 4,052,694 | 10/1977 | Fredriksson . | |
| 4,166,270 | 8/1979 | Brastins et al. . | |
| 4,233,677 | 11/1980 | Brown et al. . | |
| 4,814,711 | 3/1989 | Olsen et al. | 324/331 |
| 4,908,803 | 3/1990 | Rialan | 367/77 |
| 4,928,106 | 5/1990 | Ashjaee et al. | 342/352 |
| 5,166,905 | 11/1992 | Currie | 367/19 |
| 5,276,655 | 1/1994 | Rialan et al. | 367/77 |
| 5,301,368 | 4/1994 | Hirata | 455/78 |
| 5,523,761 | 6/1996 | Gildea | 342/357 |
| 5,568,162 | 10/1996 | Samsel et al. | 343/842 |
| 5,610,620 | 3/1997 | Stites et al. | 343/725 |
| 5,654,717 | 8/1997 | Nichols et al. | 342/357 |
| 5,668,775 | 9/1997 | Hatteland | 367/19 |
| 5,724,241 | 3/1998 | Wood et al. | 364/421 |
| 5,822,273 | 10/1998 | Bary et al. | 367/77 |
| 5,831,577 | 11/1998 | Nichols et al. | 342/357 |

OTHER PUBLICATIONS

International Search Report for PCT/US98/23136, dated Jan. 7, 1999.
Ashtech G8 GPS Board Product Brochure, Copyright ©1997 by Ashtech Inc.
Input/Output, Inc., I/O System Two®, PIB 53, Printed in USA. ©1995 Input/Output, Inc.

Primary Examiner—Mark Hellner
Attorney, Agent, or Firm—Haynes and Boone, LLP; Todd Mattingly; Tim Headley

[57] ABSTRACT

Remote seismic data acquisition unit for receiving seismic radio signals, having the capability of receiving both seismic data acquisition radio signals and GPS signals, uses a single antenna for receiving both types of signals, a signal splitter to separate the signals and a low noise amplifier to enhance the GPS signals. A GPS receiver/transmitter is incorporated within the housing for the seismic data acquisition system radio signal receiver.

12 Claims, 2 Drawing Sheets

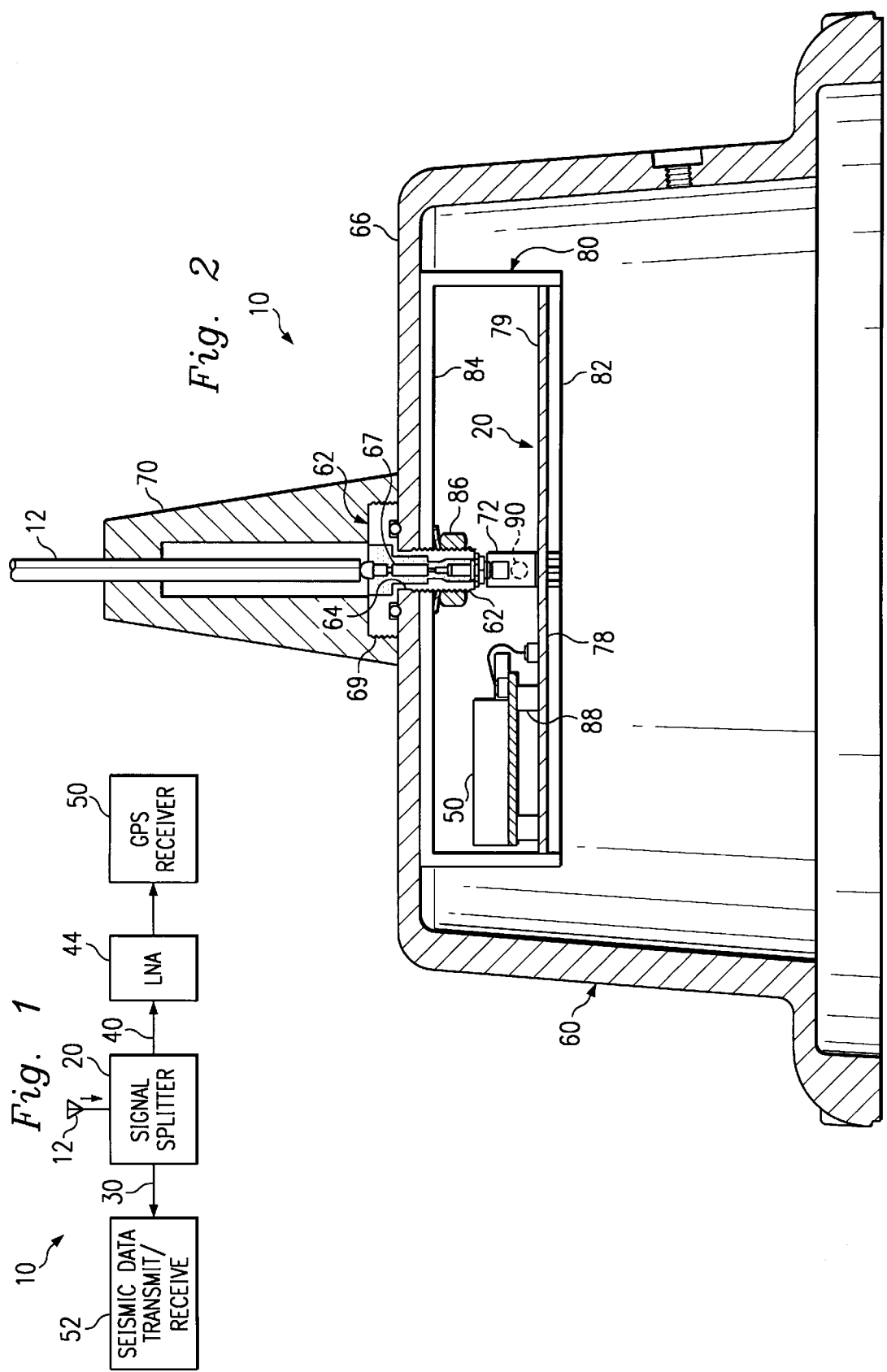

REMOTE SEISMIC DATA ACQUISITION UNIT WITH COMMON RADIO AND GPS ANTENNA

BACKGROUND OF THE INVENTION

This invention relates to radio wave receivers and in particular to receivers used to control units which gather geophysical data from remote locations.

With the ever advancing electronic data storage and data processing technology, it is possible to collect and process increasing quantities of geophysical data. Collection of data involves the use of remote seismic recorders positioned throughout the area to be seismically mapped. Each recorder unit samples, digitizes and stores seismic data in internal memory for later collection by a data collection unit which then transcribes the data to a storage medium.

There is a need for those who collect geophysical data to utilize the Ground Positioning System (GPS) information to precisely locate the source of collected data and, at the same time, to have a receiver for GPS signals that can withstand the rigors of service in often hostile environments. Remote seismic data acquisition units must be extremely durable against both shock hazards and environmental elements, particularly when used for offshore geophysical data gathering. A GPS receiver for use in connection with the gathering of geophysical data would need to be equally durable in the field.

Typically, antennas used for receiving GPS satellite signals use either a microstrip, patch, or quadrifilar antenna element for receiving the signal that contains the GPS location determination information. These types of antennas are costly and require particular housing configurations to assure that there is minimal effect of the housing on the signals being received by these antennas within the housing.

The industry needs both seismic acquisition system receivers for receiving signals in the bandwidth of about 216 to 230 mega hertz (MHz), which is available for geophysical data gathering, and receivers to receive GPS signals which are in the neighborhood of about one and a half giga hertz (1.5 GHz). It would be preferable if the reception of both could be contained in a single package that was both rugged and economical to produce.

The industry needs a global positioning system (GPS) receiver which is economical, durable and does not require a piece of equipment separate from the seismic data reception equipment. It would be advantageous to have a single antenna/receiver assembly that could provide both seismic acquisition system data and GPS data to a single software package for generating reports that include both types of data in a single report.

SUMMARY OF THE INVENTION

The present invention fulfills the needs of the industry in an economical and technically sound manner with an antenna assembly for receiving both seismic acquisition system radio signals and global positioning system (GPS) signals using only a single reception antenna extending outside the receiver.

The single reception antenna can be any type of antenna known for use in receiving radio signals in the bandwidth used for geophysical seismic acquisition system data, such as a simple whip antenna, and which acts like a long wire antenna for GPS frequencies. The antenna is mounted on a housing which is adapted to contain an enclosure for a signal frequency splitter for connection to the antenna output, a low noise amplifier for connection to the frequency splitter and a GPS signal receiver connected to the low noise amplifier.

BRIEF DESCRIPTION OF THE DRAWING

FIG. 1 is a block diagram of a preferred embodiment of the common antenna seismic and GPS receiver of the present invention.

FIG. 2 is a side cross-sectional view of a preferred embodiment of the antenna/receiver unit of the present invention.

DETAILED DESCRIPTION OF A PREFERRED EMBODIMENT

Figure 3:
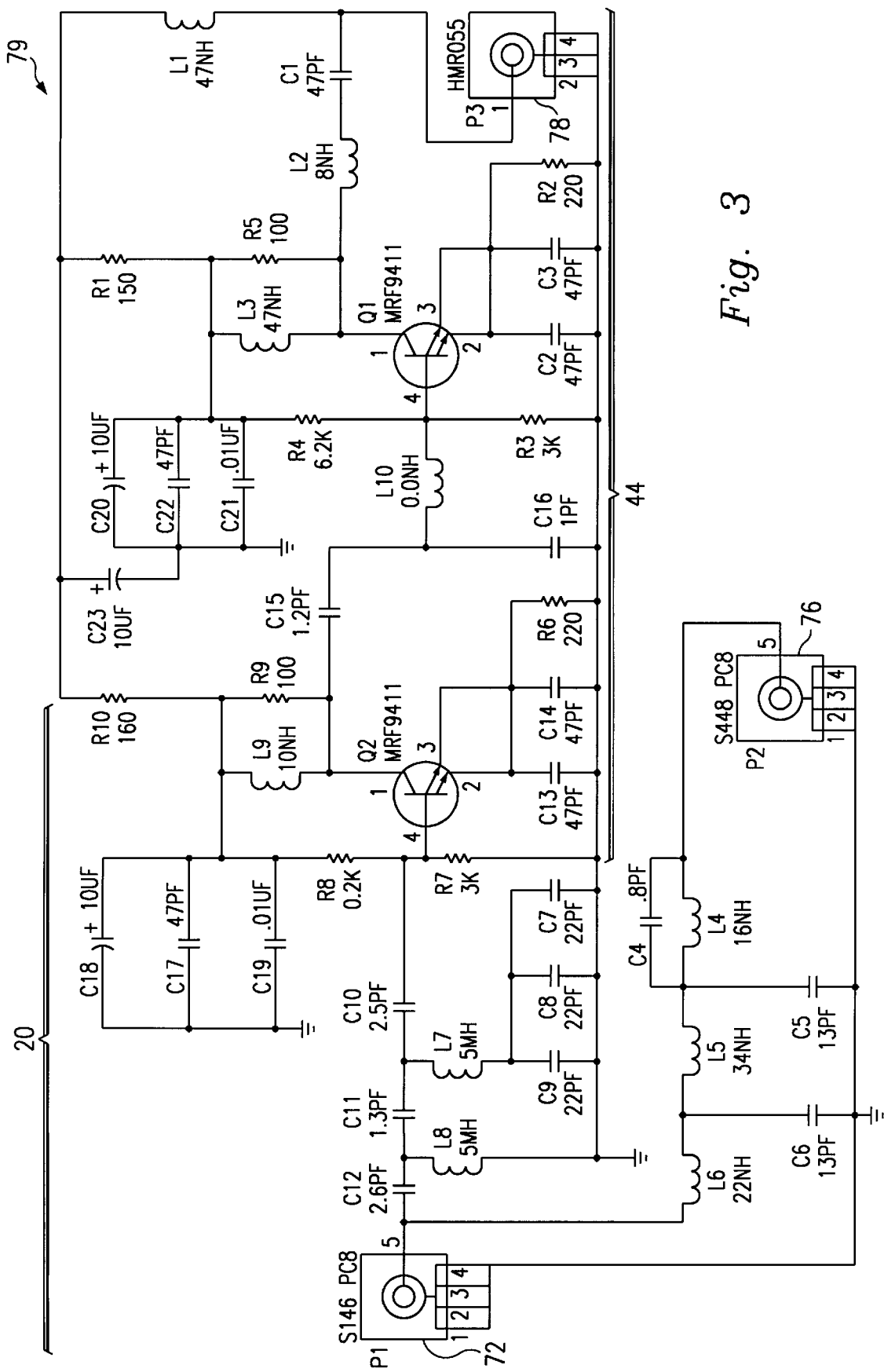
FIG. 3 is a schematic of the preferred frequency splitter shown in the block diagram of FIG. 1.

The antenna receiver assembly of the present invention incorporates in a single housing, using a single antenna, both a seismic acquisition system signal receiver and a GPS signal receiver to collect, with the use of a single unit, both GPS data and seismic acquisition system data.

Referring to FIG. 1, antenna/receiver unit 10 includes antenna 12 coupled to signal splitter 20 which splits the signals from the antenna 12 into radio signals 30 containing seismic acquisition system data and GPS signals 40 containing position data. The GPS signals 40 are fed to a low noise amplifier (LNA) 44 and then to a GPS receiver 50. The seismic acquisition system radio signals 30 are passed to a radio receiver/transmitter 52 for communications with the central electronics of the seismic data acquisition system.

With reference to FIG. 2, the antenna/receiver unit 10 of the present invention can be conveniently mounted and weatherproofed using an antenna/receiver housing 60. The housing 60 can be similar to those used to mount an antenna and enclose a remote seismic acquisition unit. A suitable remote seismic acquisition unit is the "I/O SYSTEM TWO RSR Remote Seismic Recorder" available from Input/Output, Inc. of Stafford, Tex. which is the assignee of the present invention. The housing 60 is preferably adapted to be capable of mounting to a seismic recording unit to provide the option of recording data in the field rather than retransmitting the data to a remote recording unit.

The antenna/receiver housing 60 includes a threaded mount 62 received in opening 64 in top wall 66 of the housing 60. The mount 62 includes a bore for holding antenna coupler 67 and an extended threaded upper portion 69 sized and threaded to mate with corresponding threads within antenna base 70. The antenna base 70 serves to protect the antenna 12 from damage and provide a secure mount to the housing 60. The antenna coupler 67 can be any conventional type of connector for coupling an antenna with a radio. Removably connecting the antenna and its base to the housing 60 in this manner makes the antenna/receiver unit 10 less likely to be damaged because the antenna base 70 and the antenna 12 can be easily removed and carried with the housing 60 to the remote location and only assembled when the antenna/receiver unit 10 is in its final receiving location in the field.

The antenna 12 is sized for receiving radio frequencies in a range available for seismic data acquisition systems, currently the 216 to 230 MHz range. It has been found that a whip or rod type antenna having a total length of between about one half and five eighths of a wavelength of the 216 MHz signals or about twenty-eight and a quarter inches functions as a long wire antenna and is highly effective in receiving both the seismic data acquisition system radio signals 30 and the GPS signals 40. Plug-in connector 72, also of conventional design, is provided for passing received radio and GPS signals to the splitter 20.

The signal splitter 20 as well as the low noise amplifier or LNA 44 can be of any conventional design. A preferred circuit for performing both of these functions is shown in FIG. 3. The signal splitter 20 is designed to segregate and pass signals in the 216 to 230 MHz range to radio connector 76, and signals in the 1200 to 1600 MHz range to the LNA 44 and out through GPS connector 78. A preferred circuit diagram for signal splitting and GPS signal amplification is shown in FIG. 3 as splitter/LNA board 79. The amplified GPS signals are then supplied to the GPS for signal splitting and GPS signal amplification is shown in FIG. 3 as splitter/LNA board 79. The amplified GPS signals are then supplied to the GPS receiver 50 by way of the GPS connector 78 for processing and transmission to a data acquisition and recording unit while the lower frequency radio signals are sent to the seismic data receiver/transmitter for communicating with the central electronics of the seismic data acquisition system. Either or both sets of signals can be transmitted to a remote recording unit or can be directly cabled to an on site recording unit.

Returning to FIG. 2, the GPS receiver is mounted within the housing 60 by way of enclosure 80 having the signal splitter/LNA circuit board 79 mounted on enclosure base 82. Top wall 84 of the enclosure 80 is conveniently and securely mounted within the housing 60 close to the antenna coupler 67 by providing a clearance hole in the enclosure 80 for passing the threaded mount 62 into the enclosure 80 to be secured to the housing top wall 66 by way of mounting nut 86. The GPS receiver 50 is conveniently mounted atop the circuit board 79 by way of spacers 88. The enclosure 80 is preferably sized just large enough to contain the splitter/LNA circuit board 79 and the GPS receiver. The enclosure 80 and is preferably constructed of aluminum having a wall thickness of about one tenth inch to provide light weight and appropriate electrical shielding. Mounting the enclosure 80 against the top wall 66 of the housing 60 enables the signal splitter 20 and GPS receiver 50 to be as close as possible to the antenna 12 to minimize signal losses and interference.

The GPS receiver 50 can be any commercially available receiver. For economy and performance, the GPS receiver/transmitter available from Ashtech Inc. of Sunnyvale Calif. sold as the "G8 GPS Board" is preferred. Seismic data signal output cable port 90 is conveniently provided on the plug in connector 72 for coupling with a receiver/transmitter so that the data can be either stored on site for later transportation to a data processing facility or radio transmitted to a data processing In operation, the antenna 12 receives GPS signals from global positioning system satellites and seismic data signals from seismic data sources and sends the entire set of signals through the antenna connector to the signal splitter/LNA circuit board which separates the signals into seismic data acquisition system radio signals and GPS signals. From there, the radio signals are sent to the receiver/transmitter 52 and the GPS signals to the receiver 50. From there, the data can be recorded either on site or off site on a common recording device so that both seismic and positioning information for the remote data acquisition unit can be processed together.

Although an illustrative embodiment of the invention has been shown and described, various modifications, changes and substitutions can be made without departing from the invention, the scope of which is defined by the following claims.

What is claimed is:

1. An antenna/receiver assembly for receiving and separating GPS signals from seismic data radio signals comprising:

a housing;

a single antenna mounted to the housing and designed for receiving both seismic data radio signals and GPS signals;

a frequency splitter mounted within the housing and operatively connected to the antenna and having a seismic data signal output terminal and a GPS signal output terminal;

a GPS receiver mounted within the housing and operatively connected to the GPS signal output terminal of the frequency splitter; and a radio signal connector mounted within the housing operatively connected to the geophysical data output terminal of the frequency splitter.

2. The assembly of claim 1 wherein the seismic data acquisition radio signals are in the frequency range of about 216 to about 230 MHz.

3. The assembly of claim 1 wherein the GPS signals are in the range of about 1200 to about 1600 MHz.

4. The assembly of claim 1 wherein the housing and antenna mounted thereon form a hermetically sealed unit.

5. The assembly of claim 1 wherein the antenna is designed to perform as a long wire antenna.

6. The assembly of claim 1 wherein the antenna is a whip antenna.

7. The assembly of claim 1 further comprising a low noise amplifier operatively connecting the frequency splitter to the GPS signal output terminal.

8. A method for determining the position of a remote seismic data acquisition unit comprising providing a single antenna that receives both seismic and global positioning system signals and coupling the one antenna to each of a seismic data signal receiver and a global positioning system signal receiver.

9. The method of claim 8 further comprising separating the seismic data signals from the global positioning system signals and amplifying the global positioning system signal with a low noise amplifier.

10. The method of claim 8 wherein the global positioning system signals are in the range of about 1200 to about 1600 MHz.

11. The method of claim 8 wherein the antenna is designed to perform as a long wire antenna in receiving the global positioning system signals.

12. The method of claim 11 wherein the antenna is a whip antenna.

* * * * *